United States Patent [19]
Baraket et al.

[11] Patent Number: 5,841,017
[45] Date of Patent: Nov. 24, 1998

[54] PHOTO-ACOUSTIC GAS SENSOR

[75] Inventors: Mourad Baraket, Stäfa; Mauro Feltre, Uerikon; Martin Forster, Jona; René Lenggenhager, Horgen; Andreas Portmann, Uerikon; Georges Tenchio, Ebmatingen, all of Switzerland

[73] Assignee: Cerberus AG, Mannedorf, Switzerland

[21] Appl. No.: 828,837

[22] Filed: Mar. 24, 1997

[30] Foreign Application Priority Data

Mar. 25, 1996 [EP] European Pat. Off. ............ 96104689

[51] Int. Cl.$^6$ ..................................................... G01L 27/00
[52] U.S. Cl. ............................................................. 73/1.59
[58] Field of Search ................................... 73/1.57, 1.59, 73/1.63, 1.64, 1.06, 1.71, 1.69, 25.01, 25.05, 31.01; 250/252.1, 338.5; 356/437, 243

[56] References Cited

U.S. PATENT DOCUMENTS

| | | | |
|---|---|---|---|
| 4,740,086 | 4/1988 | Oehler et al. | 356/432 |
| 4,818,882 | 4/1989 | Nexo et al. | 250/343 |
| 4,896,525 | 1/1990 | Breimesser | 73/1.88 |
| 5,402,669 | 4/1995 | Pla et al. | 73/1.59 |
| 5,479,813 | 1/1996 | Pla et al. | 73/1.59 |

OTHER PUBLICATIONS

Applied Physics Letters, Bd. 31, Nr. 11, 1, Dec. 1977, New York, US, Seiten 728–730, XP002011370. Murphy J C et al: "The Photothermophone, A Device For Absulute Calibration of Photoacoustic Spectrometers", Seite 729, linke Spalte, Zeile—rechte Spalte, Zeile 1: Abbildung 1.

*Primary Examiner*—Robert Raevis
*Attorney, Agent, or Firm*—Baker & Botts, L.L.P.

[57] ABSTRACT

In a photo-acoustic gas sensor having a measuring cell, a lamp, a photo-diode, a gas-permeable diaphragm and a microphone, a device is included for monitoring the gas-permeable diaphragm and the microphone. The device is operated in an explosion-proof manner. Intentionally, for diagnostic purposes, an artificial pressure modulation is generated in the measuring cell. The pressure modulation is converted by the microphone into electrical monitoring signals which are amplified by an amplifier circuit and assigned to preset ranges by a microprocessor, for determining the functional condition of the diaphragm and the microphone, and of microphone sensitivity. Depending on the range assigned to the monitoring signal, an output signal is generated indicating a fault in the microphone and/or the diaphragm. In the event of long-term drift in microphone sensitivity, a calibration is performed in which gas concentration values are re-calculated and stored in an EEPROM. A heater wire can be used, for modulated heating to generate the pressure modulation.

20 Claims, 5 Drawing Sheets

PHOTO-ACOUSTIC GAS SENSOR

BACKGROUND OF THE INVENTION

This invention relates to a photo-acoustic gas sensor having an active device for monitoring proper functioning of its components and calibrating its sensitivity in an explosion-proof manner, and to a method for evaluating output signals of the device.

Photo-acoustic gas sensors are used in research and industry to determine the concentration of specific prevailing gases. They are used, e.g., for process monitoring in bio-reactors and breweries, and for gas concentration monitoring in laboratories and other work areas where gas concentration levels are required not to exceed maximum permissible levels. The sensors determine the presence and concentration of gases, and generate alarm or warning signals when preset gas concentration levels are exceeded.

Known photo-acoustic gas sensors, e.g. as described in European Patent Application No. 95113854.4, typically include a measuring cell with a gas-permeable diaphragm, a light source operated in a pulsed manner, a photo-diode, a microphone, and an electrical circuit for operating the light source and microphone, and for evaluating the microphone output signal. Light pulses having characteristic wavelengths are transmitted by the light source into the measuring cell where the light is absorbed by the gas to be detected. Narrow-band light sources, e.g. light-emitting diodes and lasers, or wide-band light sources, e.g. incandescent filaments combined with optical bandpass filters are used for this purpose. The photo-diode is used to measure the intensity of the light pulses, with the resultant signals being used to regulate the operating voltage of the light source and to maintain stable light intensity. When a gas to be detected is in the vicinity of the gas sensor, the gas passes through the gas-permeable diaphragm into the measuring cell and there absorbs the light emitted into the measuring cell. Absorption of the light pulses causes the gas in the measuring cell to heat up and to expand, thereby generating a pressure modulation which is received by the microphone and converted into an electrical signal. The output signal of the microphone is amplified by an amplifier circuit and compared with gas concentration values which were stored during calibration of the sensor in a suitable memory unit, e.g. an electrically erasable programmable read-only memory (EEPROM). The concentration of the detected gas is determined on the basis of the stored calibration values. When indicated, a warning or alarm signal is generated.

If the output signal of such a gas sensor is zero, it is not clear whether this is due to absence of the gas to be detected, or to a defect in a sensor component, e.g. a change in microphone sensitivity. For passive monitoring of the functional viability of the microphone and other sensor components, the above-mentioned gas sensor provides for monitoring of a background signal component of the microphone output signal which arises due to heating of parts of the measuring cell because of light absorption. If the microphone is defective, or if the diaphragm has a small hole, the background signal becomes smaller. But the method does not permit ascertaining whether or not the microphone remains fully sensitive. If the sensitivity of the microphone has decreased, e.g. as a result of drift over time or a sudden defect, its output values will be assigned to incorrect gas concentrations, and a gas alarm may not be triggered. Furthermore, the value of the background signal depends on the wavelength of the light pulses entering the measuring cell, and is close to zero for some wavelengths, so that the background signal is difficult to evaluate.

A further method involves monitoring of microphone noise, with the disappearance of microphone noise being taken as an indication that the microphone is no longer operating properly. However, the presence of microphone noise is not a positive indicator of a properly functioning microphone. For example, noise can be caused by a defective diaphragm responding to external pressure variations, which, when superposed on sharply reduced noise of a defective microphone, can be mistaken as microphone noise. However, these monitoring methods, utilizing background signals and noise, are based on passive effects which are not under circuit control.

SUMMARY OF THE INVENTION

It is an object of the present invention to provide a photo-acoustic gas sensor including an active device for monitoring the functional viability of the gas-permeable diaphragm and microphone, as well as a method of evaluating the output signals of the monitoring device for determining the functional condition of the microphone and the diaphragm and for calibrating microphone sensitivity, and a method of operating the monitoring device. It is important that operation of the monitoring device be explosion-proof.

A preferred embodiment of the photo-acoustic gas sensor of the present invention includes a device for monitoring the functional viability of the microphone and the diaphragm, and for effecting calibration of microphone sensitivity. The monitoring device comprises a device for intentionally and actively generating in the measuring cell an "artificial" pressure modulation which is converted by the microphone into electrical monitoring signals. The monitoring device also includes an operational circuit for processing and evaluating the monitoring signals, and for calibrating the microphone sensitivity. Preferably, for generating the pressure modulation, the device comprises a heater element for modulated heating of air in the measuring cell, e.g. a wire, a resistor, a resistive heating film, an inductor coil or spiral with a suitable susceptor, or a suitable radiation source for radiative heating. The microphone housing can also be used for heating. Provided that the diaphragm is intact, modulated heating of the air generates an artificial pressure modulation which is not caused by the presence of a gas to be detected in the measuring cell of the gas sensor. If the microphone also is functioning properly, the resulting pressure modulation generates an electrical signal which is amplified and evaluated by the circuit. Suitable pressure modulation can also be generated electro-mechanically, by using a piezo-electrically actuated membrane, for example.

In a preferred method, a decision is made based on the resultant monitoring signal concerning the functional viability of the diaphragm and the microphone, and, if indicated, a calibration of the microphone sensitivity is effected. This involves evaluation of the value and the variation with time of the monitoring signal. The method involves assigning the value of a monitoring signal to one of several ranges. If the value of the monitoring signal falls within a preset nominal range, the circuit generates a signal indicating that both the diaphragm and the microphone are functioning properly. Otherwise, if the monitoring signal falls in a range above or below the nominal range, microphone sensitivity is re-calibrated by a microprocessor, e.g. by recalculating gas concentration values based on the determined microphone sensitivity and storing them in an EEPROM. If, however, the monitoring signal either exceeds or falls below preset threshold values, the circuit generates a fault signal indicating that either (1) as a result of a leaky diaphragm there was no pressure modulation in the measuring cell, or (2) the sensitivity of the microphone has dropped to zero and/or the heating element is defective.

The monitoring device is explosion proof in that the current flowing through the heating element and the maximum temperatures reached by the heating element and the components of the circuit meet safety requirements, e.g. according to European Standard EN 50020:1994 as validated by the Federal Physical-Technical Institution at Braunschweig, Germany (PTB). For example, for a wire heating element, this involves suitably selecting the material and dimensions of the wire.

DETAILED DESCRIPTION OF PREFERRED EMBODIMENTS

Figure 1:
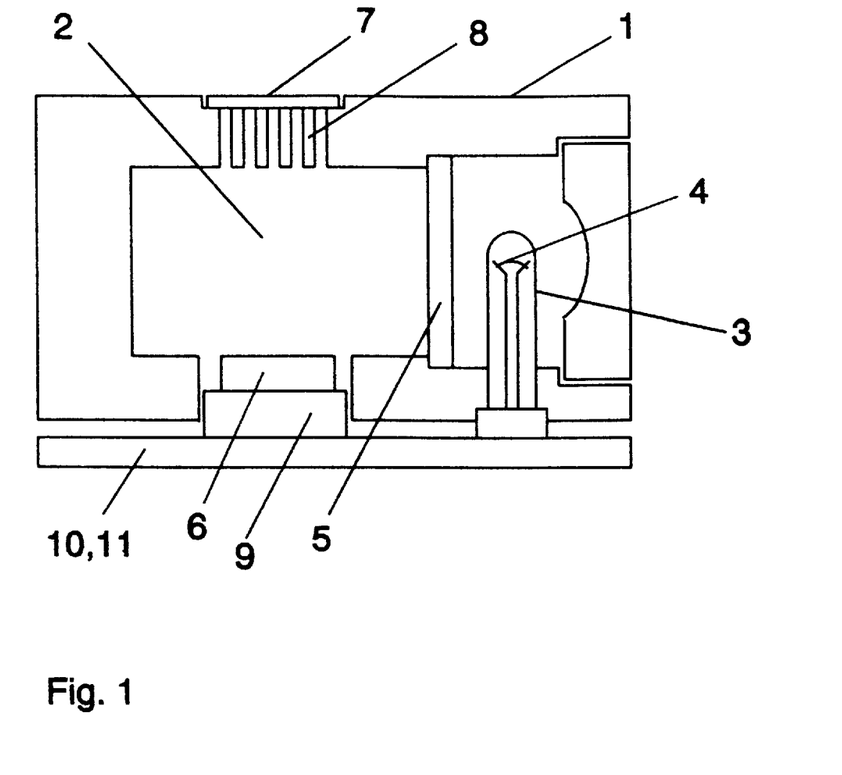
FIG. 1 is a schematic cross-section of a photoacuoustic gas sensor including a device for heating air in the measuring cell.

FIG. 1 shows a photo-acoustic gas sensor 1, having a measuring cell 2, a lamp 3 with an incandescent filament 4 as a light source and an optical bandpass filter 5, a microphone 6 and a gas-permeable diaphragm 7 disposed on a perforated grid 8 and tightly bonded by adhesive to the measuring cell wall. Not shown is a photo-diode for monitoring light intensity. The incandescent filament 4 emits wide-band light pulses that irradiate the measuring cell 2 after spectral filtering at the bandpass filter 5. For example, the optical bandpass filter 5 transmits in a narrow spectral range around the wavelength of 4.26 $\mu$m which is absorbed by $CO_2$ gas. When $CO_2$ gas is present near the gas sensor 1, the gas passes through the gas-permeable diaphragm 7 into the measuring cell 2, where it absorbs the light, heats up and expands. As a result of the expansion, a pressure modulation is generated that is detected and converted by the microphone 6 into an electrical signal. For monitoring the performance of the diaphragm 7 and the microphone 6, the gas sensor 1 includes a heating element 9 which is located at a suitable location inside the measuring cell 2. Preferably, the heating element 9 is disposed near the printed-circuit board 10 with circuit 11 which operates the gas sensor 1 and heating element 9 and which is used for evaluating the output signals of the microphone 6. The heating element 9 preferably comprises a thin wire. Also, conventional and surface-mount resistors as well as heating films are suitable for heating. Air can also be heated by electrical heating of the microphone housing. A modulated voltage is applied to the heating element 9, for heating of the heating element 9 and the air in the measuring cell 2. Expansion of the air generates a pressure modulation which is independent of the presence of any gases to be detected. The pressure modulation is converted by the microphone 6 into an electrical signal which is amplified and evaluated by the circuit 11, and a signal is generated indicating whether the microphone 6 and the diaphragm 7 are operational and/or whether the microphone sensitivity has drifted since start-up of the gas sensor 1. The heating element 9 and the components of the circuit 11 are designed and operated so as to comply with specifications for explosion-proof operation set forth by the PTB. The specifications, e.g. those of temperature classes T6 and T4 of European Standard EN 50020:1994, provide for maximum temperatures of 85° C. and 135° C., respectively. To rule out the possibility of explosion in the event of a defect in the heating element, current and voltage also have to be limited. The current limit for the heating element in the present case is 1 mA. Thus, the specifications for temperature class T6 are satisfied by the monitoring device of the gas sensor. The maximum temperature of the heating element 9 is less than 85° C. With current flow limited to 1 mA, sufficient heating of the air is achieved for monitoring purposes. This takes into account the maximum operating temperature of the gas sensor 1: when operating temperature is 60° C., the temperature of the heating element 9 may rise by no more than 25° C. The heating element 9 is chosen with a suitable resistance. In the case of a wire element, its diameter, length and material are chosen accordingly. Preferably, the material is chemically stable and has minimal resistance variation as a function of temperature, so that heat output of the wire is stable over a long period and independent of temperature. Examples of suitable materials are known by the trade names Nikrothal and Konstantan. If a material with a higher temperature coefficient of resistivity is used. instead, selecting the parameters of the wire is more difficult because the voltage applied to the heating element. then has to be regulated in accordance with wire temperature. An example of a heating element which meets the described general conditions is a wire made of Nikrothal having a diameter of 30 $\mu$m, a length of 1 cm and a resistance of 20 $\Omega$. If, at an applied voltage of 12 mV, a current of 0.6 mA flows through the wire, the wire heats up by 2.5° C. as calculated, but only 1° C. as measured. Alternatively, the wire parameters and material can be chosen for meeting the less stringent specifications of temperature class T4.

Figure 2:
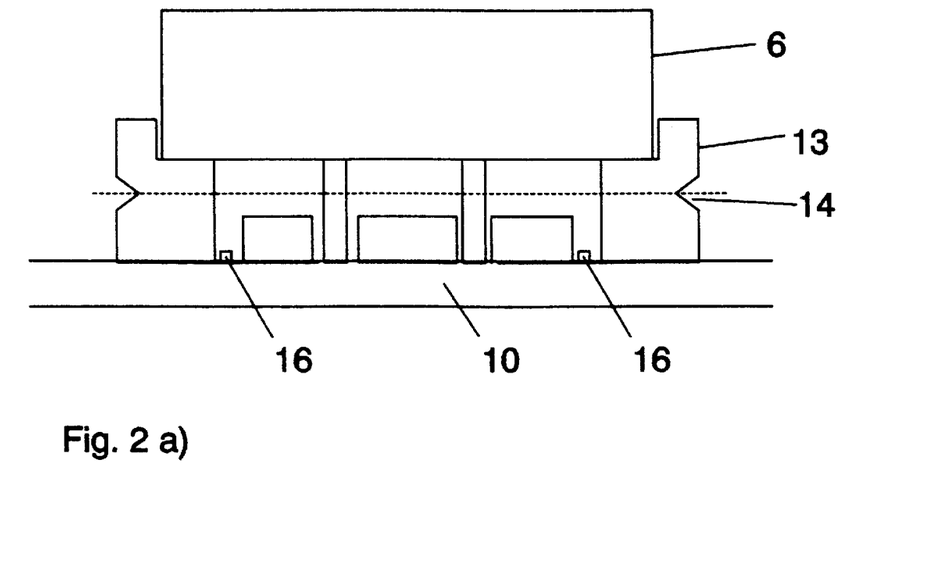
FIGS. 2a and 2b are top- and side-view schematics, respectively, of a unit including an electrical heating element for heating air in the measuring cell.

FIGS. 2a and 2b show a heating wire 12 fastened on a cylindrical carrier 13 which is attached to the microphone 6 and fastened by an adhesive to the printed-circuit board 10. To provide an air space between the microphone 6 and the wire 12, the microphone 6 is mounted on a step of the cylindrical carrier 13. At the outside of the cylindrical carrier 13 the wire is guided in a notch 14 so as to extend in, and not be displaced from, the plane indicated by the broken line, thus providing for air space below and above the wire 12 and electrically insulating the wire so that it does not contact the wall of the measuring cell 2 nor the microphone. The cylindrical carrier 13 is made of a non-conducting material, e.g., poly-carbonate. The wire 12 is wound as a meander through a plurality of slots 15 at the top edge of the cylindrical carrier 13. The ends of the wire 12 are passed through holes in the middle of the cylindrical carrier 13 and soldered by solder joints 16 on the printed-circuit board 10.

Figure 3:
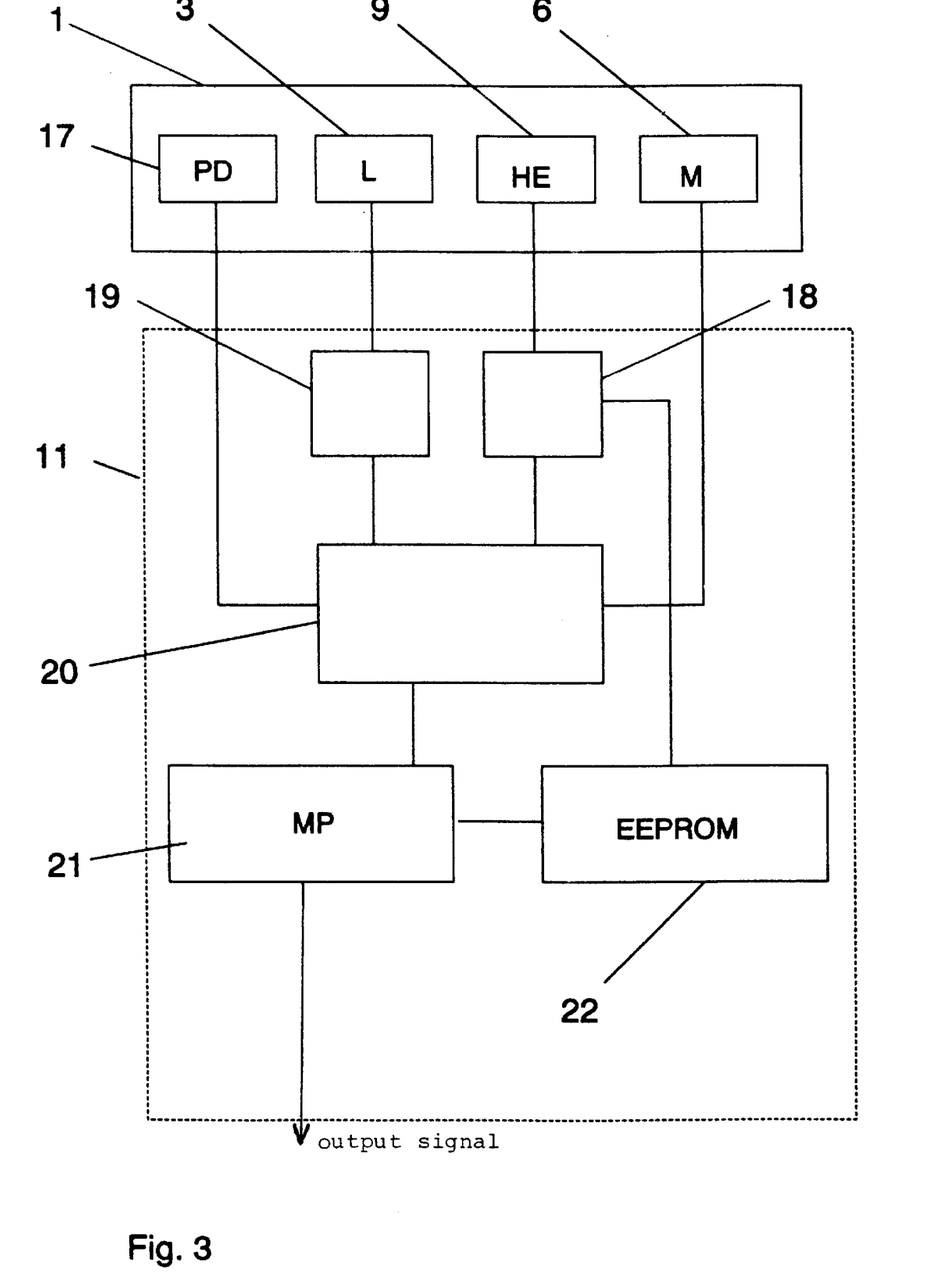
FIG. 3 is a schematic of a circuit for operating the monitoring device of the gas sensor and for evaluating the output signals of the microphone.

FIG. 3 shows electrical components of the gas sensor 1, namely a lamp 3, a microphone 6, a photo-diode 17 and a heating element 9, and the circuit 11 for operating the gas sensor 1 and the monitoring device. The circuit 11 includes a first driver circuit 18 for the heating element 9 and a second driver circuit 19 for the lamp 3. The electrical signals generated by the microphone 6 as a result. of received pressure modulations are supplied to an amplifier circuit 20 where they are linearly amplified, filtered by high- and low-pass filters, and synchronously rectified and smoothed by a phase-sensitive rectifier. The resulting DC signals are supplied to a microprocessor 21 which compares them with preset calibration values. If monitoring signal values fall within certain preset calibration ranges (see FIG. 5), it can be concluded that microphone sensitivity has changed. The change of the monitoring signal can be used in evaluations by the microprocessor 21. In the case of a slow variation, e.g., a variation over several days, this can be taken as long-term drift, and microphone sensitivity can be re-calibrated, e.g. in that the gas concentration values or the reference values stored in the EEPROM 22 are adjusted in accordance with the change in microphone sensitivity. This can be effected by determining the percentage variation of the monitoring signals and altering the gas concentration values accordingly. With compensation of the microphone sensitivity, long-term drift of the microphone is corrected. In a case of rapid variation within the calibration ranges, or when monitoring signals fall below or exceed the calibration ranges, the microprocessor generates a signal, e.g. a visual or audible signal, which indicates a fault or malfunction at the microphone and/or diaphragm.

The EEPROM 22 holds further operating data for the gas sensor such as counters, temperatures of the measured gas, brightness values of the lamp 3, and phase values for the optimum gain of the microphone output signals. The temperatures of the measured gas are determined by a temperature sensor in the amplifier circuit 20, and are used by the microprocessor 21 to recalculate the temperature-dependent gas concentration values. The brightness values of the lamp 3 are supplied by the photo-diode 17 and the amplifier circuit 20 to the microprocessor 21, and are used to regulate the light intensity of the lamp 3 in that the required pulse duration is calculated and supplied to the driver circuit 19 for the lamp 3. The phase values represent the phase differences between voltage signals for the heating element 9 and the microphone output signal. The phase values are determined in the manufacture of the gas sensor 1 in that the gain of the output signal of the microphone 6 is optimized by input of the phase. The phase at which the microphone signal reaches a maximum is then stored in the EEPROM 22.

The EEPROM 22 is a serial EEPROM with an integrated interface circuit ("IIC") bus. Because of the IIC bus, only one data line is required in addition to the clock line. The EEPROM clock also serves as a clock for the heating element 9 in that the clock signal is supplied to the first driver circuit 18 for the heating element 9.

Figure 4:
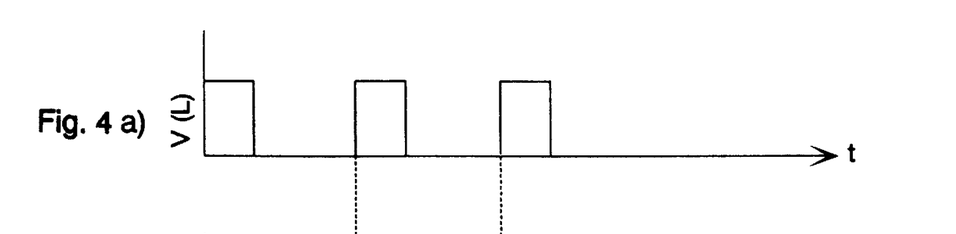
FIGS. 4a to 4e are typical timing diagrams in gas sensor monitoring and microphone sensitivity calibration.

FIG. 4a shows voltage pulses V(L) for operating the lamp 3, e.g. at 14 Hz and with an operating cycle of one third. A heating element for heating the measuring cell 2 is operated using a modulated voltage V(HE) at 7 Hz as shown in FIG. 4b, with the output curve having a clock frequency of 14 Hz. The voltage V(HE) also serves to trigger the phase-sensitive rectifier of the amplifier circuit 20. Synchronization of the lamp 3 and of the heating element 9 permits simplified evaluation of the monitoring signals and gas signals by means of the same electrical components. To minimize electrical cross-talk, the modulated voltage V(HE) preferably is sinusoidal. Suitable also are triangular or trapezoidal forms, or forms with any desired rise and fall.

FIG. 4c shows the approximate course of temperature T(HE) of a 2.5 cm long Nikrothal wire having a diameter of 30 $\mu$m, through which a current of less than 1 mA flows when the voltage of FIG. 4b is applied.

FIG. 4d shows a microphone signal V(M) generated by the microphone 6, in this case representing the electrical monitoring signal resulting from artificial heating of the measuring cell 2. The phase displacement $\Delta\phi$ of the generated signal with respect to the voltage for operating the lamp 3, stored in the EEPROM 22, is the phase determined in manufacture by optimizing the microphone signal. Signals resulting from the presence of detectable gases in the measuring cell are amplified with the same phase displacement as the monitoring signal.

FIG. 4e shows the DC output signal VOUt of the amplifier circuit 20 of the monitoring device over an extended time. In the operating example, the monitoring device is switched on and off at a frequency of $\frac{1}{10}$ Hz, avoiding permanent operation. The monitoring signal is smaller by an order of magnitude as compared with the signal resulting from gas detection, so that it can be reliably distinguished from a gas alarm signal. Over a preset period of time, e.g. 30 seconds, the mean value of the signal difference D between on and off states is determined. The mean value is definitive of the monitoring signal and is assigned by the microprocessor 21 to one of the ranges in FIG. 5.

For compactness and economy, a preferred embodiment of the photo-acoustic gas sensor has small dimensions. In a small sensor of this kind there arises the problem of electrical cross-talk between the components, more so than in larger photo-acoustic measurement devices where components can be spaced farther apart. In a small photo acoustic gas sensor, the heating element is close to the microphone. Also, to save on electrical components, the heating element and the microphone are connected to the same power supply. This can cause electrical cross-talk between the heating element and the microphone, disturbing the microphone signal V(M). For minimizing cross-talk, an additional phase shift can be used for the voltage V(HE) of FIG. 4b for operating the heating element and the resulting temperature T(HE) of FIG. 4c. The voltage for the lamp V(L) also serves to trigger the phase-sensitive rectifier of the microphone amplifier circuit 20. For optimal signal strength, and to minimize the electrical influence of the heating element on the microphone, the microphone signal V(M) is amplified with a phase shift $\Delta\phi$ with respect to V(L). The phase shift can be determined experimentally for minimized cross talk. While the voltage V(HE) is phase shifted relative to the microphone signal V(M), the electrical monitoring signal due to the artificial pressure modulation generated by the heating element is approximately in phase with the microphone signal V(M), provided the wire of the heating element is chosen with suitable thermal inertia. A wire with such thermal inertia can be chosen experimentally, for the temperature change of the heating element T(HE) and the resulting electrical monitoring signal to be approximately in phase with the microphone signal V(M). For example, if the electrical monitoring signal and the microphone signal V(M) are out of phase by just 30 degrees, then electrical cross-talk is zero, and the electrical monitoring signal is at 85% of its maximum value.

Figure 5:
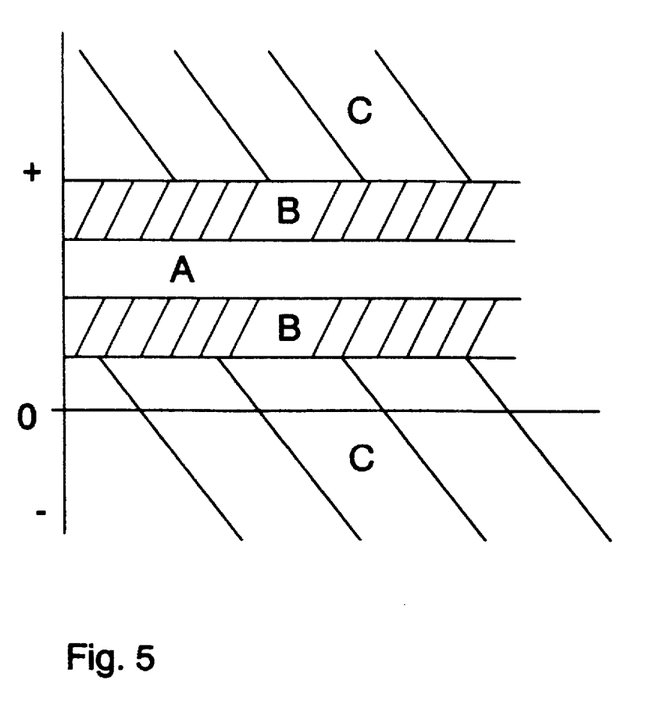
FIG. 5 is a graphic representation of signal ranges used in signal evaluation.

FIG. 5 shows three different ranges A, B and C. Depending on the range within which a mean value falls, the monitoring signal is interpreted in accordance with logic Table 1, and a corresponding signal is generated. If the mean value of the signal difference D falls within range A, a regular signal value has been obtained with an intact diaphragm and with full microphone sensitivity, and the microprocessor generates a signal indicating that the diaphragm and the microphone are functioning properly. If the mean value falls within one of the two ranges B and varies only slowly over an extended period, a re-calibration is effected to compensate for changed microphone sensitivity. If variation over time is rapid, however, what is indicated for signalling is not long-term drift but a defect or malfunction. If the mean value falls within one of the ranges C, microphone sensitivity lies outside the correctable range, and a fault signal is generated whether variation of time be slow or rapid.

TABLE 1

| Mean value of the monitoring signal | Variation over time of the mean value of the monitoring signal | Signal or action of the microprocessor MP |
| --- | --- | --- |
| A | rapid | proper functioning |
|   | slow | proper functioning |
| B | slow | re-calibration |
|   | rapid | malfunction |
| C | rapid | malfunction |
|   | slow | malfunction |

We claim:

1. A photo-acoustic gas sensor comprising:
   a measuring cell;
   a light source disposed for irradiating the measuring cell with light having a first modulation;
   a photodiode disposed for receiving radiation from the light source;
   a gas-permeable diaphragm disposed for permitting an ambient gas to enter the measuring cell;
   a microphone disposed for sensing pressure changes in the measuring cell;
   an operation/evaluation circuit operationally coupled to the light sources the photodiode and the microphone for operating the light source and evaluating signals supplied by the microphone;
   a diagnostic/calibration device comprising a pressure modulator element, configured and disposed for modulating air pressure in the measuring cell with a second modulation different from the first modulation;
   a diagnostic/calibration circuit operationally coupled to the diagnostic/calibration device for operating the diagnostic/calibration device, and to the microphone for processing and evaluating monitoring signals supplied by the microphone as a function of the modulated air pressure, for generating a signal which is indicative of the functional condition of the microphone and the diaphragm, and for calibrating microphone sensitivity.

2. The photo-acoustic gas sensor according to claim 1, wherein the operation/evaluation circuit and the diagnostic/calibration circuit are integrated together, comprising:
   a first driver circuit for operating the light source;
   a second driver circuit for operating the pressure modulator element;
   an amplifier circuit for amplifying and filtering the monitoring signals;
   a microprocessor and a memory unit, for distinguishing the monitoring signals from the evaluating signals from the microphone, for comparing the amplified monitoring signals with values preset in the memory unit, and for calculating and storing gas concentration values in the memory unit which represent microphone sensitivity.

3. The photo-acoustic gas sensor according to claim 2, wherein the memory unit comprises an EEPROM.

4. The photo-acoustic gas sensor according to claim 3, wherein the EEPROM is a serial EEPROM comprising an IIC which has an output for a clock signal which is operationally coupled to the first driver circuit.

5. The photo-acoustic gas sensor according to claim 1, wherein the pressure modulator element comprises a heater element.

6. The photo-acoustic gas sensor according to claim 5, wherein the heater element comprises a resistive element.

7. The photo-acoustic gas sensor according to claim 6, wherein the resistive element comprises a wire.

8. The photo-acoustic gas sensor according to claim 7, wherein the wire comprises a material which is selected to have a low temperature coefficient.

9. The photo-acoustic gas sensor according to claim 8, wherein the wire comprises a material selected from the group consisting of Nikrothal and Konstantan.

10. The photo-acoustic gas sensor according to claim 9, wherein the diagnostic/calibration device comprises a limiting element for limiting current flow in the wire not to exceed 1 mA and temperature of the diagnostic/calibration device including the wire not to exceed 135° C.

11. The photo-acoustic gas sensor according to claim 7, wherein the wire is disposed on a cylindrical carrier to which the microphone is attached.

12. The photo-acoustic gas sensor according to claim 11, wherein the carrier serves as a mounting for the microphone.

13. The photo-acoustic gas sensor according to claim 11, wherein the wire is conveyed through slots at a top edge of the carrier and in a notch outside at the carrier and so that an air space is formed below and above the wire.

14. The photo-acoustic gas sensor according to claim 6, wherein the resistive element comprises a resistor.

15. The photo-acoustic gas sensor according to claim 6, wherein the resistive element comprises a resistive film.

16. The photo-acoustic gas sensor according to claim 5, wherein the heater element is configured as a housing for the microphone.

17. The photo-acoustic gas sensor according to claim 5, wherein the heater element comprises an inductive element.

18. The photo-acoustic gas sensor according to claim 5, wherein the heater element comprises a radiation source.

19. The photo-acoustic gas sensor according to claim 1, wherein the pressure modulator element comprises a membrane and an electromechanical actuator for the membrane.

20. The photo-acoustic gas sensor according to claim 1, wherein said diagnostic/calibration circuit comprises processing means for determining the mean value of the monitoring signals over a time interval and for monitoring the magnitude and variation of mean values over different time intervals.

* * * * *

UNITED STATES PATENT AND TRADEMARK OFFICE
CERTIFICATE OF CORRECTION

PATENT NO. : 5,841,017

DATED : November 24, 1998

INVENTOR(S) : Baraket et al.

It is certified that error appears in the above-identified patent and that said Letters Patent is hereby corrected as shown below:

Col. 6, line 6, vout should read --$V_{out}$--;

Col. 7, line 30, "light sources" should read --light source,--.

Signed and Sealed this

Twentieth Day of July, 1999

Attest:

Q. TODD DICKINSON

*Attesting Officer*     *Acting Commissioner of Patents and Trademarks*